United States Patent [19]

Kaufman et al.

[11] Patent Number: 5,141,854
[45] Date of Patent: Aug. 25, 1992

[54] ENZYMATIC COMPOSITION FOR ETHANOL ASSAY

[75] Inventors: Richard A. Kaufman, Belleville; Henry J. Rosenfeld, Florham Park, both of N.J.

[73] Assignee: Hoffman-La Roche, Inc., Nutley, N.J.

[21] Appl. No.: 628,080

[22] Filed: Dec. 13, 1990

[51] Int. Cl.$^5$ ............................ C12G 1/32; C12N 9/04
[52] U.S. Cl. ........................................ 435/26; 435/190
[58] Field of Search ................................ 435/26, 190

[56] References Cited

U.S. PATENT DOCUMENTS

| | | | |
|---|---|---|---|
| 3,926,736 | 12/1975 | Bucolo | 435/26 |
| 3,941,659 | 3/1976 | Koch et al. | 435/26 |
| 4,481,292 | 11/1984 | Raymond | 435/147 |
| 4,810,633 | 3/1989 | Bauer et al. | 435/25 |

OTHER PUBLICATIONS

Clinical Chemistry, 24(6), 873 (1976).
Z. Lebensm. Unters. Forsch., 168, 112 (1979).
Clinical Chemistry, 28(10), 2125 (1982).
J. Pharmaceut. Biomed., 4(5), 545 (1986).
Meth. Enzymatic Anal., Bergmeyer, H., ed., 2nd Ed., vol. 3, pp. 1499–1502.
Meth. Enzymatic Anal., Bergmeyer H., ed., 3rd. Ed., vol. 6, pp. 598–601 (1984).

Primary Examiner—Douglas W. Robinson
Assistant Examiner—Maarian C. Knode
Attorney, Agent, or Firm—George M. Gould; George W. Johnston; Alan P. Kass

[57] ABSTRACT

An enzymatic assay composition for ethanol determination is provided. A compound of the formula $$H_2N-(CH_2)_n-CHR-CH_2-NH_2$$

where
R is H, $CH_3$, or OH and
N is 0–4 acts as a buffer and a trapping agent for a product of the enzymatic reaction. Long stability of the assay composition is achieved.

12 Claims, No Drawings

ENZYMATIC COMPOSITION FOR ETHANOL ASSAY

BACKGROUND OF THE INVENTION

1. Field of the Invention

This invention relates to a composition for ethanol assay.

2. Description

The testing of body fluids, such as saliva, blood, and urine, for determining the amount of ethanol therein is important for safety and health reasons, among others. Abuse of alcohol and detection thereof together with determination of blood alcohol content when a person is suspected of driving while intoxicated are two of many important areas where quick and reliable ethanol determination is important.

A useful method of determining the ethanol content of body fluids utilizes the enzymatic reaction whereby ethanol is converted to acetaldehyde by the action of alcohol dehydrogenase (ADH) and where nicotinamide adenine dinucleotide (NAD), acting as a coenzyme, is converted to its reduced form (NADH), as shown in the reaction sequence below:

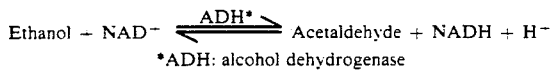

*ADH: alcohol dehydrogenase

The equilibrium of this reaction lies on the side of ethanol and NAD. However, the equilibrium is displaced to the right when the reaction takes place under alkaline conditions and the acetaldehyde formed is trapped. The course and extent of the reaction can be determined by spectrophotometric resolution at 340 nanometers. At this wavelength, NAD does not absorb ultraviolet light, but NADH does absorb ultraviolet light. The amount of NADH formed in the above reaction corresponds to the amount of ethanol present.

To be used as an assay, the reaction must go to completion. However, because of the unfavorable equilibrium of the reaction when ethanol is oxidized to acetaldehyde by NAD, the acetaldehyde has to be removed from the system so that NADH is quantitatively formed with respect to the ethanol. One way to remove, or trap, the acetaldehyde is to use a trapping agent. Additionally, as with most enzymatic reactions, a buffer is necessary to maintain the pH of the assay system within the optimum range for the particular enzymatic reaction.

It is also known that trapping agents presently used can inactivate ADH. Current assay systems have low stability once mixed, less than one day at room temperature (about 20° C.) and about 3 days if refrigerated. Fresh assay reagents must be prepared frequently and low stability may lead to a more frequent need to run known ethanol samples to ensure accuracy.

Many traping agents currently used in ethanol assays and reagents, for example, hydrazine, can inactivate ADH, limiting the shelf stability of the assay or reagent.

Thus, there exists the need for a trapping agent that does not inactivate ADH. There also exists need for an enzyme stabilizing composition for the ADH. There also exists the need for an assay system which has long stability.

SUMMARY OF THE INVENTION

The present invention relates to a composition for assaying ethanol. The composition includes enzyme alcohol dehydrogenase, coenzyme nicotinamide adenine dinucleotide, and a compound of the formula $$H_2N-(CH_2)_n-CHR-CH_2-NH_2 \qquad I$$

where R is H, $CH_3$, or OH, and n is 0, 1, 2, 3, or 4. Suitable compounds of formula I include 1,2-diaminoethane (R=H;n=0), 1,2-diaminopropane (R=$CH_3$;n=0), 1,3-diaminopropane (R=H;n=1), and 1,3-diamino-2-hydroxypropane (R=OH;n=1). Preferably, the composition further comprises an enzyme stabilizing composition for ADH.

The compounds of formula I are effective buffers at a pH of about 9 in an aqueous solution. At this pH, the compounds of formula I are useful in that they simultaneously exhibit good buffering capacity and trapping effect to trap the acetaldehyde formed in the reaction sequence discussed hereinabove.

DETAILED DESCRIPTION OF THE INVENTION

The present invention relates to a composition for assaying ethanol. The composition comprises enzyme alcohol dehydrogenase, coenzyme nicotinamide adenine dinucleotide, and a compound of the formula $$H_2N-(CH_2)_n-CHR-CH_2-NH_2 \qquad I$$

where R is H, $CH_3$ or OH and n is 0, 1, 2, 3, or 4. Suitable compounds of formula I include 1,2-diaminoethane (R=H;n=0), 1,2-diaminopropane (R=$CH_3$;n=0), 1,3-diaminopropane (R=H;n=1), and 1,3-diamino-2-hydroxypropane (R=OH;n=1). Preferably, the composition further comprises an enzyme stabilizing composition for the ADH.

The compounds of formula I are effective buffers at a pH of about 9 in an aqueous solution. At this pH, the compounds of formula I are useful in that they simultaneously exhibit good buffering capacity and trapping effect to trap the acetaldehyde formed in the reaction sequence discussed hereinabove. It has been found that 1,3-diamino-2- hydroxypropane helps to stabilize the ADH.

Another aspect of the present invention is to enhance the stability of the composition. Applicants have found that the present invention provides for increased stability. The invention herein, quite unexpectedly, has been found to form a stable composition having stability, that is, the ADH is not inactivated, of at least about 60 days at 4° C.

The individual components that comprise the assay can be put together by usual methods well known in the art. For example, the components can be intimately mixed, using conventional techniques, to form an aqueous solution. In a preferred embodiment, enhanced stability of the composition is obtained by first forming two separate reagents, a primary reagent and a start reagent, which later can be mixed together, by conventional techniques, to form an assay composition prior to use. Conveniently, the primary reagent comprises the compound of formula I, and the start reagent comprises the NAD, the ADH and the enzyme stabilizer composition for the ADH. The pH of the primary reagent is preferably in the range of about 8.5 to about 9.5. The pH of the start reagent is preferably in the range of about 6.5 to about 7.0.

The invention can be used as follows:

A preselected amount of primary reagent is placed into three separate reaction cuvettes. A fixed volume of sample is then introduced to each cuvette. To the first cuvette is added water; this reaction, after addition of the start reagent, as discussed below, will serve as the reagent blank. The same volume of a known ethanol standard solution is added to the second cuvette. Finally, the last cuvette will receive the same volume of a sample of unknown ethanol content. Absorbance readings at 340 nm are then taken for all three cuvettes, thus generating the sample blanks.

A preselected amount of start reagent is added to each of the first, second, and third cuvettes. Preferably, the ratio of volume of primary reagent to volume of start reagent is about 3:1. The cuvettes are then incubated at a temperature from about 25° C. to about 40° C.

During the incubation, further spectrophotometric readings are taken until the end point of the reaction is determined. The endpoint of the reaction is that point where all of the ethanol is oxidized to acetaldehyde. The resulting data are analyzed and the amount of ethanol in the sample fluid containing ethanol is determined. The assay composition is well suited for automated testing equipment but can be used with any spectrophotometer capable of measuring ultraviolet absorbance in the range of from about 320 nm to about 380 nm.

It is also possible to manually premix preselected amounts of the primary reagent and the start reagent to form a single working reagent, which is then pipetted into a cuvette by an automated clinical analyzer. The same ratio of primary reagent volume to start reagent volume is used.

Both the primary reagent and the start reagent can contain a preservative. Those of ordinary skill in the art will appreciate that the preservatives which are useful are those preservatives which are effective in the prevention of microbial growth in a pH environment of greater than or equal to 6. A preferred preservative is sodium azide.

The primary reagent can also contain an acid which reduces the unadjusted pH of the primary reagent to a pH range of about 8.5 to about 9.5. In this pH range, the compound of formula I acts as a trapping agent and also acts as a buffer for the primary reagent.

The start reagent can also contain an enzyme stabilizing composition (ESC) as mentioned above. The ESC is useful in maintaining the active configuration of the ADH such that the ADH does not denature. The ESC can conveniently contain one or more compounds. Since it is well known in the art that ADH contains zinc and sulfhydryl (i.e., thiol, or —SH) moieties, compounds containing zinc and/or sulfhydryl moieties are preferable candidates. Preferably, the zinc compounds, for example zinc salts, are capable of ionizing to yield free zinc ions. One example of such a compound is zinc sulfate. Preferably, the sulfhydryl containing compounds contain at least one sufhydryl group attached to an organic radical whose type and structure are well known to those of ordinary skill in the art. One example of such compound is 1-thioglycerol.

In addition, the ESC can contain salts of methanesulfonic acid derived from alkali metals, for example, sodium or potassium, or from alkaline earth metals, such as magnesium. The ESC can also contain D-mannitol.

The ESC can optionally contain other compounds that help to stabilize the ADH. This compound can also act as a buffer for the start reagent. The start reagent should be buffered to ensure that the stability of the ADH and NAD are maintained. It is known in the art that ADH will retain enzymatic activity in a pH range of about 6.5 to about 8.5. It is also known that NAD hydrolyzes at a faster rate in an alkaline environment than in an acidic environment. Thus, it is preferable that the buffer be able to maintain the pH of the start reagent from about 6.5 to about 7.0, and preferably at a pH of about 6.8. Conveniently, an acid and a base, or the salt of the acid, can be used. An example of such an acid salt is sodium citrate.

Preferred compounds and concentration ranges which comprise the primary reagent and the start reagent are set forth below:

|  | RANGE |
| --- | --- |
| PRIMARY REAGENT | |
| Compound of formula I | 0.1–1.0 mol/L |
| Sodium Azide | 0.01–1% |
| START REAGENT | |
| Sodium Citrate | 1.0–100.0 mmol/l |
| Sodium Azide | 0.01–1% |
| Zinc Sulfate | 0–10.0 mmol/L |
| 1-Thioglycerol | 0–1.0 mmol/L |
| Methanesulfonic Acid, Sodium Salt | 0–5.0 mmol/L |
| D-Mannitol | 0–15.0% |
| NAD | >4.0 mmol/L |
| ADH | >10.0 KU[1]/L |

[1]KU = 1000 units

The invention herein is more fully described in the Example below and the Example is not meant to limit the scope of the invention. Unless otherwise stated, all percentages are weight per volume. All temperatures are degrees Celsius.

EXAMPLE

The purpose of this experiment was to determine the concentration of ethanol in a sample fluid using a composition of the present invention.

1,3-diamino-2-hydroxypropane, at a concentration of 0.3 mol/L, and sodium azide, at a concentration of 0.1% of the total solution, were intimately mixed together to form a primary reagent having an adjusted pH of about 9.

The following compounds were mixed together to form a start reagent:

| a) sodium citrate | 50 mmol/L |
| --- | --- |
| b) sodium azide | 0.1% |
| c) zinc sulfate | 1.0 mmol/L |
| d) 1-thioglycerol | 0.25 mol/L |
| e) methanesulfonic acid, sodium salt | 2.5 mol/L |
| f) D-mannitol | 10.0% |
| g) NAD | 36.0 mmol/L |
| h) ADH | 360 KU/L |

The analysis of a sample fluid containing ethanol ("sample fluid") was performed on a COBAS MIRA ® clinical chemistry analyzer (available from Roche Diagnostics, Inc.) in accordance with standard operating procedures.

In this Example, 120 μL of the primary reagent, 2 μL of the sample fluid and 90 μL of water, to flush out the sample probe, were pipetted into a reaction cuvette (Cycle 1 of the COBAS MIRA ®). An absorbance reading at 340 nm was taken, which served as the sample fluid blank. In addition, an ethanol standard, having a known concentration of ethanol, was also pipetted into a cuvette together with the same amount of primary reagent. An absorbance reading at 340 nm was taken, which served as the blank for the ethanol standard. Then, 40 μL of start reagent and 55 μL of water were added to the reaction cuvettes (Cycle 2 of the COBAS MIRA ®). A reagent blank containing 120 μL of primary reagent, 147 μL of water, and 40 μL of start reagent was also formed in a cuvette. The cuvettes were incubated at 37° C. for several additional cycles until the absorbance at 340 nm reached an endpoint, that is, the oxidation of ethanol to acetaldehyde was completed. The calculation of ethanol in the sample fluid containing ethanol is based on the difference in absorbance readings taken at the end of Cycle 1 and at the end of Cycle 6. One cycle equals 25 seconds. The difference in absorbance readings is proportional to the ethanol concentration in the sample fluid containing ethanol.

The reagent blank had an absorbance at 340 nm ($A_{340}$) of 0.41 and the ethanol solution standard (300 mg/dL) had an $A_{340}$ of 1.98. The sample fluid blank had an $A_{340}$ of 0.00. The sample fluid had an $A_{340}$ of 0.84. The COBAS MIRA ® calculated the ethanol concentration in the sample fluid to be 83 mg/dL. The COBAS MIRA ® calculated the ethanol concentration by taking the ratio of the corrected absorbance for the sample fluid tested to the corrected absorbance of the ethanol standard and multiplying the result times the ethanol standard concentration, yielding the ethanol concentration of the sample fluid. The corrected absorbance was the absolute absorbance corrected for the reagent blank and the sample fluid blank absorbance readings.

As discussed above, increased stability of the composition has been found. Increased stability of a composition was determined using a COBAS MIRA ® as follows:

A 3:1 proportional solution of primary reagent to start reagent was prepared to form a single working reagent. 200 μL of the single working reagent, 2 μL of sample containing ethanol and 50 μL of diluent (water) were pipetted into a reaction cuvette. An $A_{340}$ reading was immediately taken (at 4.5 sec. after mixing). This reading is equivalent to the sample blank in the Example hereinabove. The reaction cuvette was incubated at 37° C. until the endpoint was reached (about 6 min. or 15 cycles). As was the case in the above Example, a reagent blank and an ethanol standard were also run.

A known sample containing ethanol having a concentration of 380 mg/dL was assayed each time the single working reagent was tested. Between tests, the single working reagent was kept in a refrigerator at 4° C. The known sample containing ethanol was assayed at 17, 30, 60, and 90 days. If the sample still assayed at (or recovered) an ethanol concentration of approximately 380 mg/dL, stability of the single working reagent was determined to be maintained.

The calculations were performed on the COBAS MIRA ® in the same manner as discussed in the Example above. The results of the stability test are presented below:

Stability at 4° C. of Single Working Reagent

Recovery of sample containing ethanol at a concentration of about 380 mg/dL

Days at 4° C. (Single Working Reagent)

| | 17 | 30 | 60 | 90 |
|---|---|---|---|---|
| Assay value (mg/dL) | 381 | 387 | 383 | 371 |

We claim:
1. An assay solution for determining ethanol content in a body fluid comprising:
   (a) enzyme alcohol dehydrogenase;
   (b) coenzyme nicotinamide adenine dinucleotide; and
   (c) a compound in an amount sufficient to prevent interference by acetaldehyde, said compound having the formula

$$H_2N-(CH_2)_n-CHR-CH_2-NH_2$$

where R is H, CH$_3$, or OH; and n is 0, 1, 2, 3, or 4.
2. The composition of claim 1 which further comprises an enzyme stabilizing solution for the enzyme alcohol dehydrogenase wherein said stabilizing solution comprises a zinc compound, a sulfhydryl containing compound, a salt of methanesulfonic acid, D-mannitol, or a salt of citric acid.
3. The composition of claim 2 wherein the pH of the composition is within a range of about 8.5 to about 9.5.
4. The composition of claim 3 wherein the compound is selected from the group consisting of $$H_2N-CH_2-CH_2-NH_2;$$

$$H_2N-CH_2-CH_2-CH_2-NH_2;$$

$$H_2N-CH(CH_3)-CH_2-NH_2; \text{ and}$$

$$H_2-CH_2-CH(OH)-CH_2-NH_2.$$

5. The composition of claim 4 wherein the compound is $H_2N-CH_2-CH(OH)-CH_2-NH_2$.
6. The composition of claim 2 wherein said enzyme stabilizing solution comprises zinc sulfate, 1-thioglycerol, sodium salt of methanesulfonic acid, D-mannitol and sodium citrate.
7. A composition comprising:
   (a) enzyme alcohol dehydrogenase;
   (b) coenzyme nicotinamide adenine dinucleotide; and
   (c) a compound of the formula $$H_2N-(CH_2)_n-CHR-CH_2-NH_2 \qquad I$$

wherein R is H, CH$_3$, or OH; and n is 0, 1, 2, 3, or 4.
8. The composition of claim 7 which further comprises an enzyme stabilizing composition for the enzyme alcohol dehydrogenase wherein said stabilizing composition comprises a zinc compound, a sulfhydryl containing compound, a salt of methanesulfonic acid, D-mannitol, or a salt of citric acid.
9. The composition of claim 8 wherein the pH of the composition is within a range of about 8.5 to about 9.5.
10. The composition of claim 9 wherein the compound is selected from the group consisting of $$H_2N-CH_2-CH_2-NH_2;$$

$$H_2N-CH_2-CH_2-CH_2-NH_2;$$

$$H_2N-CH(CH_3)-CH_2-NH_2; \text{ and}$$

-continued $H_2-CH_2-CH(OH)-CH_2-NH_2.$

11. The composition of claim 10 wherein the compound is $H_2N-CH_2-CH(OH)-CH_2-NH_2$.

12. The composition of claim 8 wherein the enzyme stabilizing composition comprises zinc sulfate, 1-thiogylcerol, sodium salt of methanesulfonic acid, D-mannitol and sodium citrate.

* * * * *

UNITED STATES PATENT AND TRADEMARK OFFICE
CERTIFICATE OF CORRECTION

PATENT NO.  : 5,141,854
DATED       : August 25, 1992
INVENTOR(S) : Richard A. Kaufman and Henry J. Rosenfeld It is certified that error appears in the above-identified patent and that said Letters Patent is hereby corrected as shown below:

Claim 1, column 6, delete whole claim 1 and insert therefor whole claim 7;

In claim 4, column 6, line 37, delete "$H_2$" and insert therefor -- $H_2N$ --;

Claim 7, column 6, delete whole claim 7 and insert therefor whole claim 1;

In claim 10, column 7, line 1, delete "$H_2$" and insert therefor -- $H_2N$ --.

Signed and Sealed this

Fourth Day of April, 1995

Attest:

BRUCE LEHMAN

*Attesting Officer*  *Commissioner of Patents and Trademarks*